United States Patent
Shiroshita et al.

(10) Patent No.: US 10,429,358 B2
(45) Date of Patent: Oct. 1, 2019

(54) METHOD AND APPARATUS FOR INSPECTING DELAMINATION OF LAMINATED BODY

(71) Applicant: NON-DESTRUCTIVE INSPECTION COMPANY LIMITED., Osaka (JP)

(72) Inventors: Satoru Shiroshita, Osaka (JP); Ryusuke Tanaka, Osaka (JP); Masashi Mori, Osaka (JP)

(73) Assignee: NON-DESTRUCTIVE INSPECTION COMPANY LIMITED., Osaka (JP)

(*) Notice: Subject to any disclaimer, the term of this patent is extended or adjusted under 35 U.S.C. 154(b) by 0 days.

(21) Appl. No.: 16/095,213

(22) PCT Filed: Apr. 5, 2017

(86) PCT No.: PCT/JP2017/014208
§ 371 (c)(1),
(2) Date: Oct. 19, 2018

(87) PCT Pub. No.: WO2017/187911
PCT Pub. Date: Nov. 2, 2017

(65) Prior Publication Data
US 2019/0137456 A1 May 9, 2019

(30) Foreign Application Priority Data
Apr. 25, 2016 (JP) .................. 2016-086847

(51) Int. Cl.
*G01N 29/48* (2006.01)
*G01N 29/11* (2006.01)
(Continued)

(52) U.S. Cl.
CPC ........... *G01N 29/48* (2013.01); *G01N 29/041* (2013.01); *G01N 29/043* (2013.01); *G01N 29/11* (2013.01);
(Continued)

(58) Field of Classification Search
CPC ...... G01N 29/48; G01N 29/041; G01N 29/11; G01N 29/4427
See application file for complete search history.

(56) References Cited

U.S. PATENT DOCUMENTS

2008/0229834 A1* 9/2008 Bossi ................ G01N 29/11
73/627
2011/0239769 A1 10/2011 Schmitt et al.
(Continued)

FOREIGN PATENT DOCUMENTS

JP S58-160865 A 9/1983
JP 2006-276032 A 10/2006
(Continued)

OTHER PUBLICATIONS

International Search Report issued in Application No. PCT/JP2017/014208, dated May 30, 2017.

*Primary Examiner* — David Z Huang
(74) *Attorney, Agent, or Firm* — Michael Best & Friedrich LLP

(57) ABSTRACT

An object is to provide a delamination inspection method and a delamination inspection apparatus capable of easily and distinctly detecting an inter-layer delamination of a laminated body even when an obstacle such as a reinforcing plate is present on a part to be inspected, and capable of inspecting a wide inspection area in a short time. The apparatus includes: a transmission probe 2a that causes an ultrasonic wave to enter a laminated body 10 at a predetermined refraction angle θ; a reception probe 2b that receives a propagation wave having propagated while having been repeatedly reflected by interfaces of a plurality of members; and a probe holding means that holds the transmission probe 2a and the reception probe 2b with a predetermined interval L therebetween. A propagation wave having propagated through a sound part is received, and a detection length over (Continued)

which the echo height of the received propagation wave is detected as being equal to or greater than a predetermined value is obtained as a reference detection length. The propagation wave having propagated through an inspection target part E is received, and a detection length over which the echo height of the received propagation wave is detected as being equal to or greater than the predetermined value is measured. The measured detection length is compared with the reference detection length to inspect whether or not an inter-layer delamination D is present in the inspection target part E.

18 Claims, 10 Drawing Sheets

(51) Int. Cl.
*G01N 29/04* (2006.01)
*G01N 29/44* (2006.01)

(52) U.S. Cl.
CPC . *G01N 29/4427* (2013.01); *G01N 2291/0231* (2013.01); *G01N 2291/044* (2013.01); *G01N 2291/2634* (2013.01); *G01N 2291/2695* (2013.01)

(56) References Cited

U.S. PATENT DOCUMENTS

| 2017/0140256 A1 | 5/2017 | Kobata et al. |
| 2017/0350999 A1* | 12/2017 | Merciu ............... E21B 47/00 |

FOREIGN PATENT DOCUMENTS

| JP | 2008-164394 A | 7/2008 |
| JP | 3161399 U | 7/2010 |
| JP | 5624250 B2 | 11/2014 |
| WO | WO-2013/161834 A1 | 10/2013 |
| WO | WO-2015/174374 A1 | 11/2015 |

* cited by examiner (a)

(b)

(c)

(d)

METHOD AND APPARATUS FOR INSPECTING DELAMINATION OF LAMINATED BODY

TECHNICAL FIELD

The present invention relates to a method and an apparatus for inspecting delamination of a laminated body. Specifically, the present invention relates to a method and an apparatus for inspecting delamination of a laminated body, in which an ultrasonic wave is caused to enter a laminated body obtained by laminating a plurality of members, from a sensor disposed on one side of the laminated body, the ultrasonic wave having propagated through the laminated body is received, and the received ultrasonic wave is evaluated to inspect whether or not an inter-layer delamination is present.

BACKGROUND ART

Conventionally, targets to be subjected to an inspection for delamination in a laminated body are mostly pipes, containers, and the like. When the inspection is performed, usually, a person enters a pipe, a container, or the like, and performs a visual inspection, a hammering test, a pinhole inspection, etc. from the inside. Therefore, operations have to be suspended during the inspection, and the inspection takes a lot of time.

Meanwhile, as an example of the aforementioned inspection method, Patent Document 1 has proposed a method of inspecting peeling of a lining without suspending the operation. The method disclosed in Patent Document 1 includes: causing an ultrasonic wave pulse to enter a pipe or a container from the outside; obtaining a region in which a variation range for each number of reflections of multiple reflection in a sound part does not overlap a variation range for each number of reflections of multiple reflection in an artificial delamination part; obtaining the number of reflections of a reflected wave, which is greater than the smallest number of reflections in the obtained region and at which the height of the region is equal to or greater than a predetermined value; receiving a multiple-reflected wave in an inspection portion of the laminated body; and comparing the received multiple-reflected wave with an echo height of a reflected wave in the sound part, obtained in advance, which is equal to or greater than a predetermined value, thereby inspecting whether or not an inter-layer delamination is present.

In the aforementioned method, however, if an obstacle such as a reinforcing plate is present on the inspection portion, a probe cannot be disposed on the surface of a test body, resulting in a region that cannot be inspected. Meanwhile, when a test region having a wide area is inspected, the entire surface of the test region needs to be scanned with a probe, resulting in an increase in the inspection time, and an increase in costs for the inspection.

CITATION LIST

Patent Documents

[PATENT DOCUMENT 1] Japanese Patent No. 5624250

SUMMARY OF THE INVENTION

Problems to be Solved by the Invention

The present invention is made in view of the aforementioned circumstances of the conventional arts, and an object of the present invention is to provide a delamination inspection method and a delamination inspection apparatus that are capable of easily and distinctly detecting an inter-layer delamination of a laminated body even when an obstacle such as a reinforcing plate is present on a part to be inspected, and capable of inspecting a wide inspection area in a short time.

Solution to the Problems

In order to achieve the above object, a delamination inspection method according to the present invention is a method including: causing an ultrasonic wave to enter a laminated body obtained by laminating a plurality of members, from a sensor disposed on one side of the laminated body; receiving the ultrasonic wave having propagated through the laminated body; and evaluating the received ultrasonic wave to inspect whether or not an inter-layer delamination is present. In this method, the sensor includes: a transmission probe configured to cause the ultrasonic wave to enter the laminated body at a predetermined refraction angle; a reception probe configured to receive a propagation wave having propagated while having been repeatedly reflected by interfaces of the plurality of members; and a probe holding means configured to hold the transmission probe and the reception probe with a predetermined interval therebetween. The method includes: disposing the transmission probe and the reception probe on a sound part of the laminated body, with a preset probe interval therebetween by using the probe holding means, receiving the propagation wave having propagated through the sound part, and obtaining, as a reference detection length, a detection length over which an echo height of the received propagation wave is detected as being equal to or greater than a predetermined value; disposing the transmission probe and the reception probe so as to sandwich an inspection target part of the laminated body with an interval same as the preset probe interval by using the probe holding means, receiving the propagation wave having propagated through the inspection target part, and measuring a detection length over which an echo height of the received propagation wave is detected as being equal to or greater than a predetermined value; and comparing the measured detection length with the reference detection length to inspect whether or not an inter-layer delamination is present in the inspection target part.

According to the above configuration, the sensor includes the probe holding means configured to hold the transmission probe that causes the ultrasonic wave to enter the laminated body at the predetermined refraction angle, and the reception probe that receives the propagation wave having propagated while having been repeatedly reflected by the interfaces of the plurality of members, with the predetermined interval therebetween. Therefore, an area (probe interval) between the transmission probe and the reception probe becomes an inspection area, and a wide area can be subjected to an inspection at a time. Then, by using the probe holding means, the transmission probe and the reception probe are disposed so as to sandwich the inspection target part of the laminated body with an interval same as the preset probe interval. Then, the propagation wave having propagated through the inspection target part is received, and the detection length over which the echo height of the received propagation wave is detected as being equal to or greater than a predetermined value is measured. Then, the measured detection length is compared with the reference detection length that has been obtained in the sound part in advance. Since the sound pressure reflection coefficient at the interface in the sound part in which the adjacent members are closely adhered (are in close contact) with each other is smaller than the sound pressure reflection coefficient of air, the ultrasonic wave (propagation wave) is attenuated due to reflection, transmission, or the like at the interface. On the other hand, when a delamination part is present in the inspection target part, the ultrasonic wave (propagation wave) does not transmit the delamination part (air), and attenuation thereof due to reflection hardly occurs. Thus, the propagation wave propagating between the probes has less degree of attenuation in the delamination part than in the sound part as long as the probe interval is constant, and therefore, the range over which the echo height is equal to or greater than the predetermined value is longer in the received waveform in the delamination part than in the received waveform in the sound part. Accordingly, whether or not an inter-layer delamination is present in the inspection target part can be easily and distinctly detected by comparing the detection length measured in the inspection target part, with the reference detection length, obtained in the sound part in advance, over which the echo height of the propagation wave is equal to or greater than the predetermined value.

The transmission probe and the reception probe are desirably disposed so as to sandwich another member provided on the laminated body. Thus, whether or not a delamination is present directly beneath the other member can be easily inspected.

Each of the transmission probe and the reception probe is preferably a longitudinal wave angle probe. When the longitudinal wave angle probe is used, since not only a longitudinal wave but also a transverse wave is present in the inspection target part at the same time, various modes of ultrasonic waves are propagated through the inspection target part, whereby the difference in signals becomes more distinct.

The sensor desirably further includes a scanning means configured to cause the transmission probe and the reception probe to scan the laminated body. Thus, a wider inspection target part can be speedily inspected. The scanning direction may be either a direction Va intersecting (perpendicular to) a direction in which the transmission probe and the reception probe oppose each other (ultrasonic wave propagating direction) as shown in FIG. 6, for example, or a direction Vb identical to the probe opposing direction (ultrasonic wave propagating direction) as shown in FIG. 10, for example.

The sensor may further include a first scanning means configured to cause the transmission probe and the reception probe to scan along a first scanning direction, and a second scanning means configured to scan along a second scanning direction intersecting the first scanning direction, and the position of the inter-layer delamination may be specified through the scanning of the first scanning means and the second scanning means. Since scanning not only in one direction but also in different two directions can be performed, it is possible to calculate the position of an inter-layer delamination that is present in the inspection target part between the transmission probe and the reception probe in an overlapping scanning portion as shown in FIG. 16, for example.

Furthermore, in any of the aforementioned configurations, a scanning image may be generated based on the propagation wave having propagated through the inspection target part. Thus, identification of the difference in signals (presence/absence of an inter-layer delamination) is facilitated.

The transmission probe and the reception probe may be disposed on a curved surface of the laminated body. In this case, at least the transmission probe may be a normal probe, and the transmission probe may be disposed on the curved surface of the laminated body. Then, the transmission probe may be fixed to the top of the curved surface while the reception probe may be caused to scan in a circumferential direction with respect to the transmission probe. Thus, inspection of the inspection target part at the curved surface can be efficiently performed with the simple structure. In any of the aforementioned configurations, the laminated body may be a mirror plate portion of a container. Alternatively, the laminated body may be a tubular body.

The plurality of members may include at least a first member positioned at the one side, a second member provided on the first member, and an adhesive layer adhering these members. In this case, the first member may be a steel member, and the second member may be a lining member. The first member may be a lining member, and the second member may be a steel member.

In order to achieve the above object, a delamination inspection apparatus for a laminated body according to the present invention includes a signal processing unit configured to cause an ultrasonic wave to enter a laminated body obtained by laminating a plurality of members, from a sensor disposed on one side of the laminated body, receive the ultrasonic wave having propagated through the laminated body, and evaluate the received ultrasonic wave to inspect whether or not an inter-layer delamination is present. In this configuration, the sensor includes: a transmission probe configured to cause the ultrasonic wave to enter the laminated body at a predetermined refraction angle; a reception probe configured to receive a propagation wave having propagated while having been repeatedly reflected by interfaces of the plurality of members; and a probe holding means configured to hold the transmission probe and the reception probe with a predetermined interval therebetween. The signal processing unit is configured to: dispose the transmission probe and the reception probe on a sound part of the laminated body in advance, with a preset probe interval therebetween by using the probe holding means, receive the propagation wave having propagated through the sound part, and obtain a detection length, as a reference detection length, over which an echo height of the received propagation wave is detected as being equal to or greater than a predetermined value; dispose the transmission probe and the reception probe so as to sandwich an inspection target part of the laminated body with an interval same as the preset probe interval by using the probe holding means, receive the propagation wave having propagated through the inspection target part, and measure a detection length over which an echo height of the received propagation wave is detected as being equal to or greater than a predetermined value; and compare the measured detection length with the reference detection length to inspect whether or not an inter-layer delamination is present in the inspection target part.

The signal processing unit may generate a scanning image on the basis of the propagation wave having propagated through the inspection target part. Examples of the scanning image include a B-scope image and a C-scope image.

Advantageous Effects of the Invention

According to the features of the delamination inspection method and apparatus for a laminated body according to the present invention, even when an obstacle such as a reinforcing plate is present on a part to be inspected, an inter-layer delamination of a laminated body can be easily and distinctly detected, and thus even a wide inspection area can be inspected in a short time.

Other objects, configurations, and effects of the present invention will become apparent from the following description of embodiments of the invention.

DESCRIPTION OF EMBODIMENTS

Next, the present invention will be described in more detail with reference to FIGS. 1 to 6.

Figure 1:
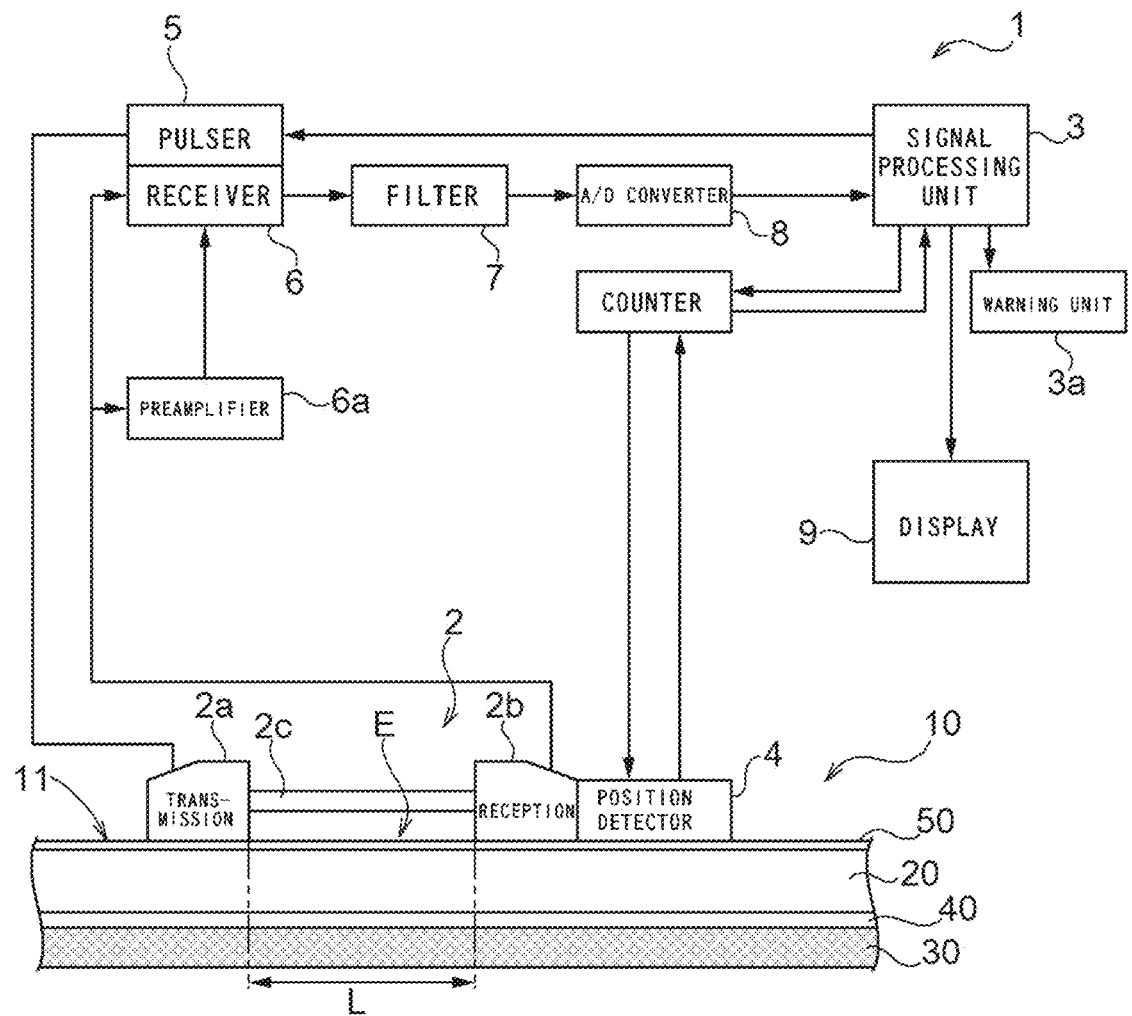
FIG. 1 is a schematic view of a delamination inspection apparatus according to the present invention.

As shown in FIG. 1, a delamination inspection apparatus 1 according to the present invention roughly includes: a sensor 2 that scans one side 11 (surface) of a laminated body 10 described later; and a signal processing unit 3 that controls the sensor 2, and processes and evaluates a received ultrasonic wave. The signal processing unit 3 is composed of a personal computer, for example.

The sensor 2 includes: a transmission probe 2a that causes an ultrasonic wave to enter the laminated body 10 at a predetermined refraction angle; a reception probe 2b that receives a propagation wave having propagated while having been repeatedly reflected by interfaces of members in the laminated body 10; and a probe holding means 2c that holds the transmission probe 2a and the reception probe 2b with a predetermined interval therebetween. A scanning means 4, including a position detector such as an encoder for detecting a scanning position, is mounted to the sensor 2, and the sensor 2 is connected to the signal processing unit 3. In the present invention, a region (probe interval L) sandwiched by the transmission probe 2a and the reception probe 2b can be an inspection target part E.

As for the transmission probe 2a and the reception probe 2b, a longitudinal wave angle probe is used, for example. The probe holding means 2c may be formed of a rod-shaped body as shown in FIG. 1, a plate-shaped body, or the like. Alternatively, the probe holding means 2c may be configured to substantially maintain the probe interval L by, for example, synchronous control via an encoder or the like. Any scanning means 4 may be used as long as it is movable in one direction (scanning direction) while maintaining the probe interval L between the transmission probe 2a and the reception probe 2b.

The signal processing unit 3 controls a pulser 5 to cause an ultrasonic wave pulse to be generated from the transmission probe 2a. The transmitted ultrasonic wave pulse passes (or transmits) through members 20, 30, and 40 of the laminated body 10 while being reflected by the interfaces of the members, and is received by the reception probe 2b. The received ultrasonic wave (propagation wave) is amplified by a receiver 6 and/or a preamplifier 6a, is subjected to noise removal by a filter 7, and is converted into a digital signal by an A/D converter 8. Then, the digital signal is subjected to signal processing by the signal processing unit 3, and is displayed on a display 9.

The signal processing unit 3 processes the received signal together with data of the scanning position of the sensor 2, which has been detected by the position detector of the scanning means 4, to generate scanning images such as a B-scope image and a C-scope image, and causes the display 9 to display the scanning images. Further, the signal processing unit 3 may be provided with a warning means 3a that warns that delamination is present.

Figure 2:
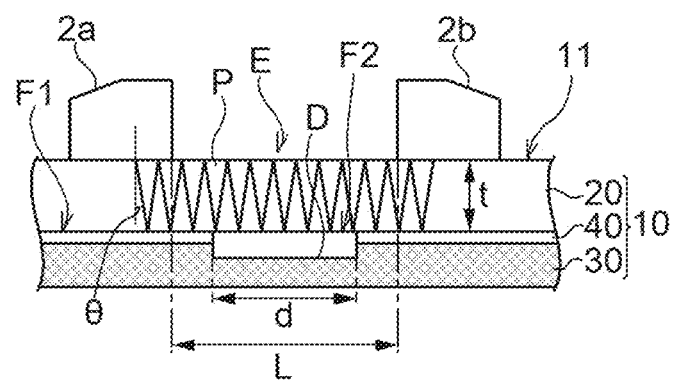
FIG. 2 is a diagram for describing the behavior of an ultrasonic wave.

As shown in FIGS. 1 and 2, the laminated body 10 that is to be an inspection target includes, for example, a plate member as a first member 20, and a lining member as a second member 30 that is adhered to the plate member 20 via an adhesive layer 40 made of an adhesive. The laminated body 10 is a pipe, a tank, or the like, for example. As for the members of the laminated body 10, for example, the plate member 20 may be a stainless steel sheet (SUS sheet), the lining member 30 may be a fluororesin lining (PTFE), and the adhesive layer 40 may be an epoxy-resin-based adhesive. However, the members are not limited to these materials. Although a coating film 50 is formed on the surface side 11 of the plate member 20, the present invention is applicable regardless of presence/absence of the coating film 50.

Next, behavior (propagation) of the ultrasonic wave that has entered the laminated body 10 will be described.

As shown in FIG. 2, in a sound part, in which the plate member 20, the lining member 30, and the adhesive layer 40 are closely adhered to each other and no delamination is present, within the probe interval L between the transmission probe 2a and the reception probe 2b, most of the ultrasonic wave having entered at a refraction angle θ is reflected by an interface F1 and propagates in the plate member 20. However, part of the ultrasonic wave enters the lining member 30 and propagates in the lining member 30.

In addition, since a sound pressure reflection coefficient of the interface F1 formed by the plate member 20 and the adhesive layer 40 is smaller than 1, the ultrasonic wave is attenuated due to the reflection at the interface F1.

On the other hand, if a delamination part D is present between the plate member 20 and the adhesive layer 40, the ultrasonic wave reflected and propagated in the plate member 20 is reflected by an interface F2 with air in the delamination part D. Since a sound pressure reflection coefficient of air in the delamination part D is approximately 1, the ultrasonic wave is not substantially attenuated even when being repeatedly reflected.

Figure 3:
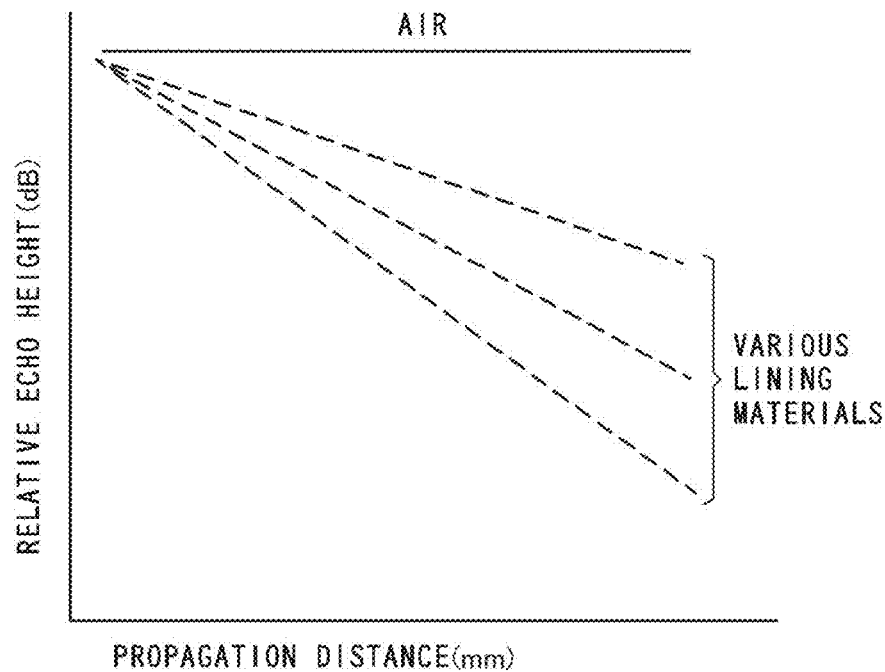
FIG. 3 is a graph schematically showing the relationship between a relative echo height and a propagation distance with repeated reflections in a sound part (delamination-free part).
Figure 4:
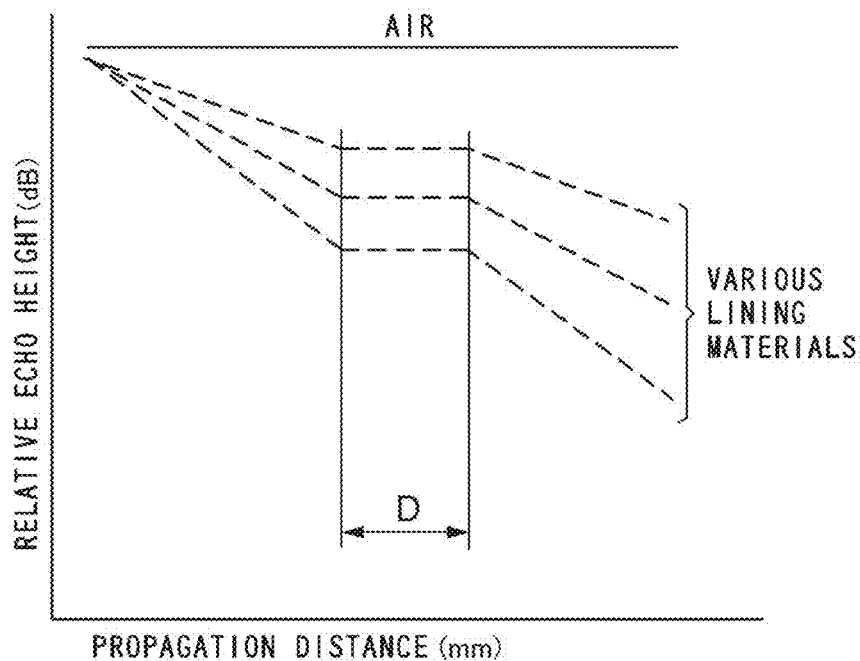
FIG. 4 is a graph, similar to FIG. 3, in an area having a delamination part.
Figure 5:
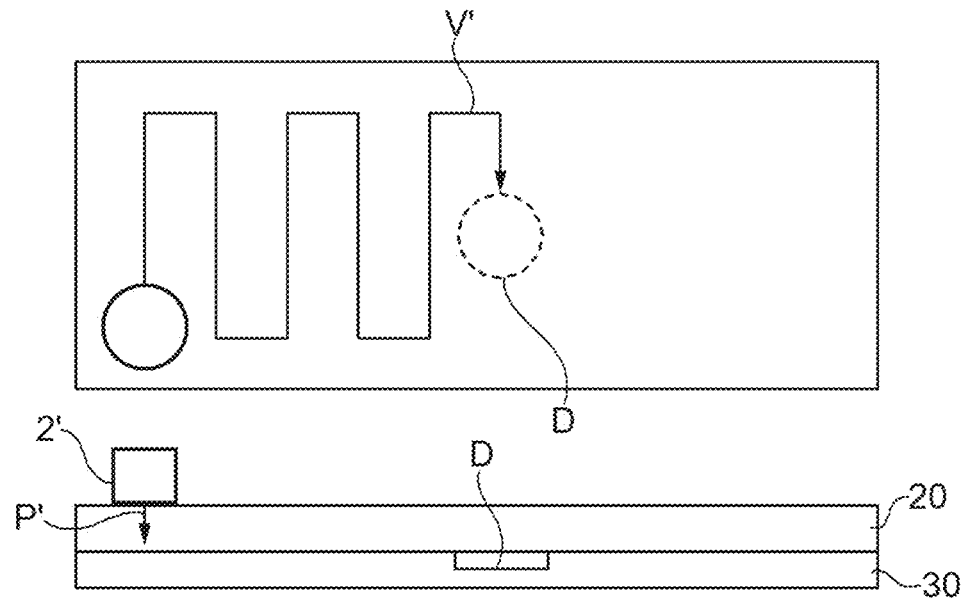
FIG. 5 is a diagram for describing an inspection (scanning) according to the conventional normal beam technique.

FIGS. 3 and 4 schematically show changes in sound pressure reflection coefficients of various materials, with respect to perpendicular incidence of an ultrasonic wave. The vertical axis indicates a relative echo height (dB), and the horizontal axis indicates a propagation distance with repeated reflections (referred to simply as "propagation distance" on the horizontal axis in each figure and in the following description). Although the sound pressure reflection coefficient varies depending on the material, the sound pressure reflection coefficient of each material is smaller than the sound pressure reflection coefficient of air (approximately 1) of air, and a difference therebetween increases as the propagation distance increases with an increase in the number of reflections. When the delamination part D is absent (in other words, in the sound part), the ultrasonic wave is attenuated due to transmission and/or reflection at the interface F1 with the adjacent member. Meanwhile, when the delamination part D is present, since the reflection at the interface F1 in the sound part is replaced with the reflection at the interface F2 with the air in the delamination part D, attenuation due to reflection hardly occurs in the delamination part D. In addition, since no transmission occurs in the delamination part D, there is no adverse effect caused by attenuation due to transmission. Therefore, as shown in FIGS. 3 and 4, the difference in echo height becomes greater in the sound part than in the delamination part, as the propagation distance increases with an increase in the number of reflections. Moreover, since the ultrasonic wave is reflected by the air in the delamination part D, the echo height is not lowered in the delamination part D. Therefore, it is conceivable that, when the delamination part D is present, the range, over which the echo appears, becomes longer than that in the sound part. Further, as the refraction angle θ of the ultrasonic wave is smaller, the number of reflections at the interface F1 in the propagation path increases, and accordingly, the number of reflections at the interface F2 with the air in the delamination part D also increases, whereby the difference in signals between the sound part and the delamination part becomes more distinct.

As described above, when the signal of the propagation wave in the sound part is compared with that in the area having the delamination part, with the probe interval L as the ultrasonic wave propagation distance being constant, the length (range) over which the signal appears as being equal to or greater than a predetermined echo height (signal intensity) is shorter (smaller) in the sound part having more attenuation than in the area having the delamination part. Accordingly, the delamination part D can be detected by: obtaining, as a reference detection length, a detection length over which the echo height of the propagation wave is detected as being equal to or greater than a predetermined value in the sound part; and comparing a detection length, over which the echo height of the propagation wave is detected as being equal to or greater than the predetermined value in the inspection target part E, with the reference detection length. The detection length is represented as a distance (time period) from a propagation position (time) at which the echo height of the received propagation wave firstly becomes equal to or greater than the predetermined value to a propagation position (time) at which the echo height lastly becomes equal to or greater than the predetermined value.

Next, the procedure of the delamination inspection method will be described with the laminated body 10 as an example.

Figure 7:
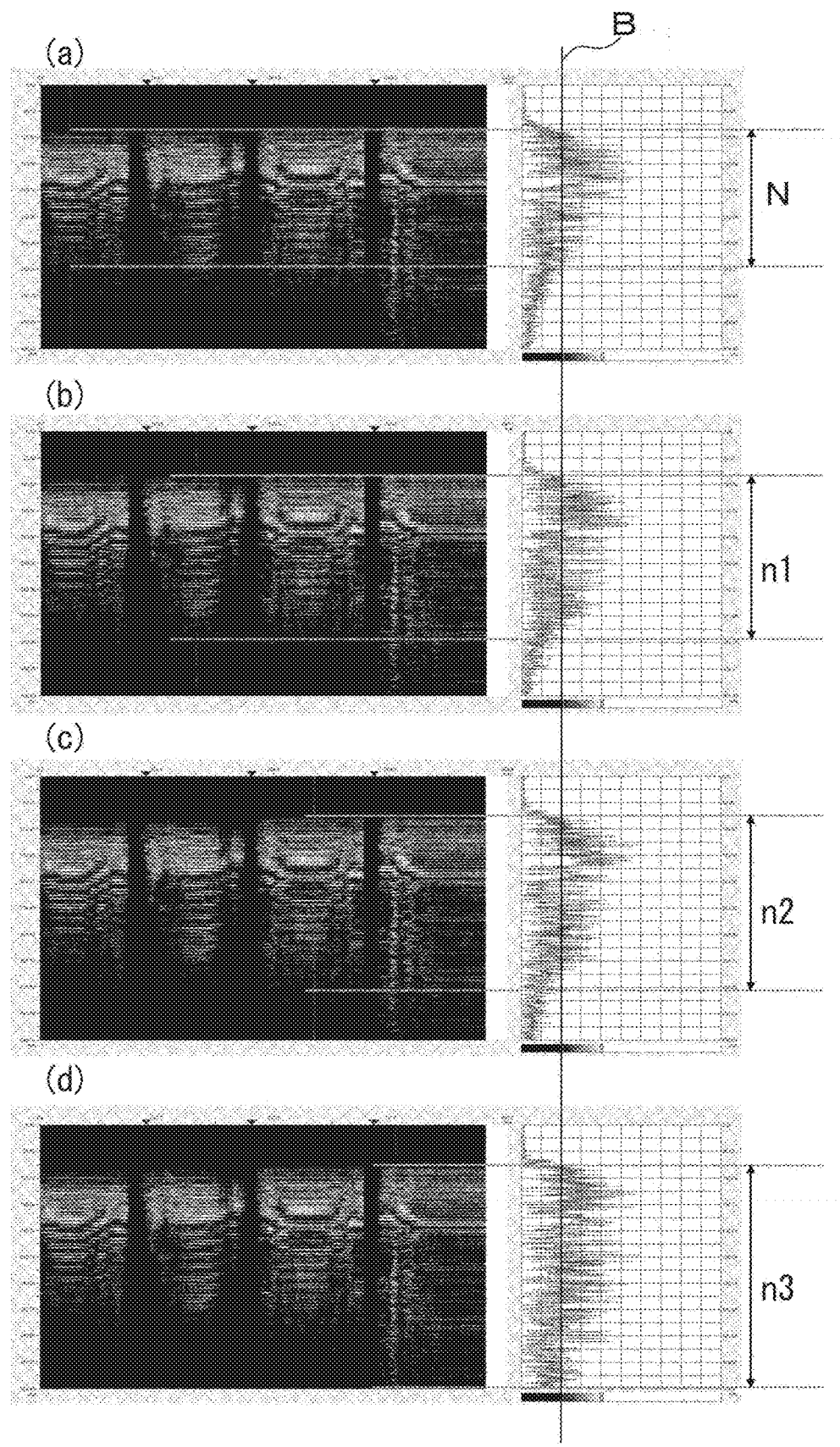
FIG. 7 is a diagram showing measurement results of a polyethylene lining test body, wherein (a) shows a delamination width of 0 mm (sound part), (b) shows a delamination width of 20 mm, (c) shows a delamination width of 50 mm, and (d) shows a delamination width of 100 mm.

First, the transmission probe 2a and the reception probe 2b, having a preset probe interval L therebetween, is disposed by using the probe holding means 2c on the sound part of the laminated body 10 in which the plate member 20, the lining member 30, and the adhesive layer 40 are closely adhered to each other. Then, an ultrasonic wave is caused to enter the laminated body 10 from the surface of the plate member 20 at a refraction angle θ, and a propagation wave having propagated through the probe interval L is received. Then, as shown in, for example, (a) of FIG. 7, a detection length over which the echo height of the received propagation wave is detected as being equal to or greater than a predetermined value is obtained as a reference detection length N, and stored in the signal processing unit 3. The probe interval L is a distance (length) that is arbitrarily set in advance. The predetermined value of the echo height is also arbitrarily set in advance as a reference value. In the example of FIG. 7, a signal intensity corresponding to an echo height equal to or greater than 20% of 100% amplitude display that appears on the display 9, is used as a reference.

In determining the reference detection length N, as described above, the sensor 2 is placed on the sound part of the laminated body 10. However, the present invention is not limited thereto. A sound test body separated from the laminated body 10 or any other device or member equivalent to the sound test body may be used. Thus, since the "sound part" is a "part", this "part" includes both "an arbitrary portion of the laminated body 10 to be an inspection target" and "a test body (specimen) separated from the laminated body 10 and any other device or member equivalent to the test body".

Next, by using the probe holding means 2c, the transmission probe 2a and the reception probe 2b are disposed so as to sandwich the inspection target part E of the laminated body 10 with the same probe interval L as described above, and a propagation wave having propagated through the inspection target part E is received. Then, as shown in, for example, (a) of FIG. 7, a detection length n is measured, over which the echo height of the received propagation wave is detected as being equal to or greater than a predetermined value. The predetermined value in this case is the same as the predetermined value (reference value) set for the measurement in the sound part. Then, the measured detection length n is compared with the reference detection length N obtained in advance. When the detection length n is longer than the reference detection length N, it is determined that an inter-layer delamination D is present between the transmission probe 2a and the reception probe 2b (in the inspection target part E).

Figure 6:
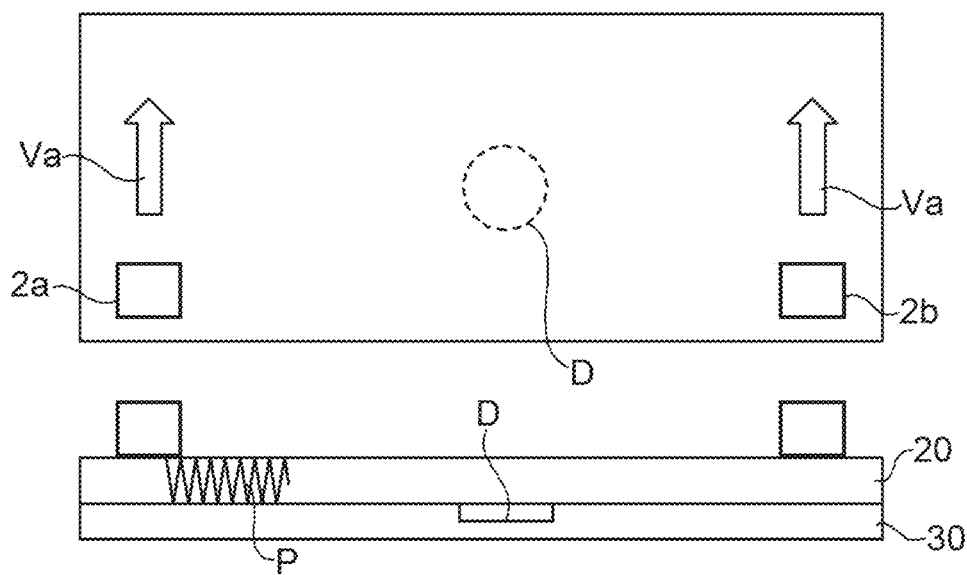
FIG. 6 is a diagram for describing a delamination inspection (scanning) according to the present invention.

Since the inspection is performed with the transmission probe 2a and the reception probe 2b being held by the probe holding means 2c while maintaining the preset probe interval L, even if there is an obstacle between the transmission probe 2a and the reception probe 2b, it is possible to inspect whether or not a delamination is present directly beneath the obstacle. Moreover, in the conventional normal beam technique, square scanning (FIG. 5) is needed to inspect the entire surface of the inspection target part. However, in the present invention, since scanning is performed with the probe interval L being maintained by the probe holding means 2c, only one-direction scanning is needed as shown in FIG. 6, thereby significantly reducing the inspection time, leading to improved inspection efficiency.

When it is determined that the inter-layer delamination D is present, a warning may be provided by the warning means 3a. Of course, the propagation wave may be processed together with the scanning position data from the position detector of the scanning means 4, and scanning images such as a B-scope image and a C-scope image may be generated and displayed together with or independently from graphs, for example. Presence/absence of delamination may be displayed in these images.

Figure 8:
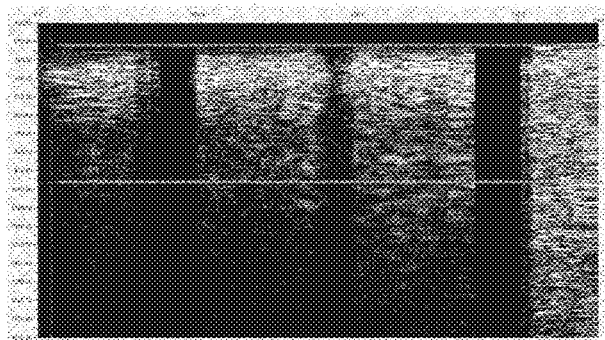
FIG. 8 is a diagram, similar to FIG. 7, regarding a polyethylene lining test body with a patch plate.
Figure 8:
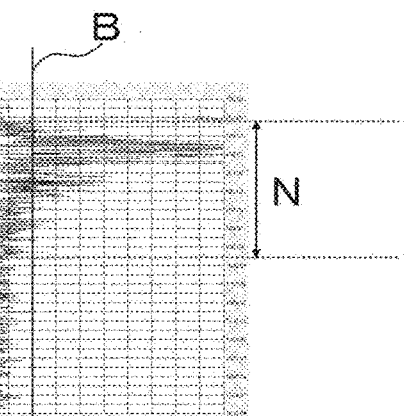
Figure 8:
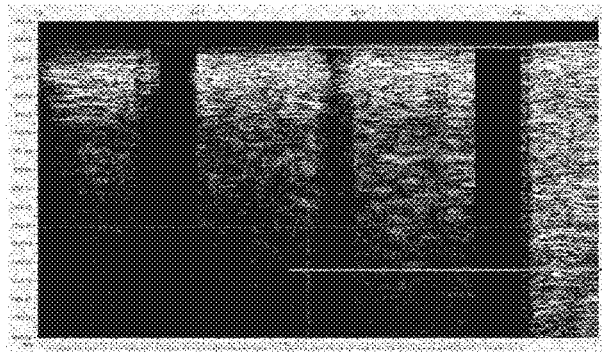
Figure 8:
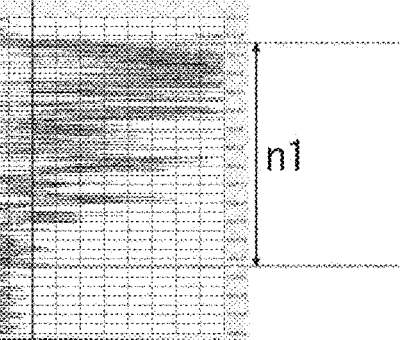
Figure 8:
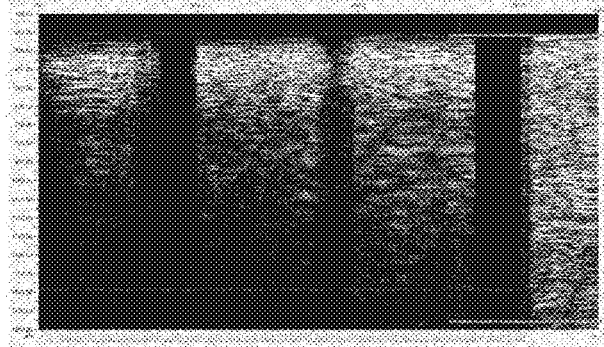
Figure 8:
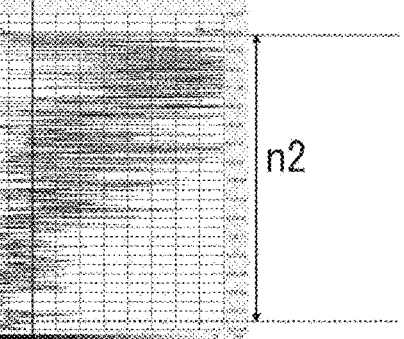
Figure 8:
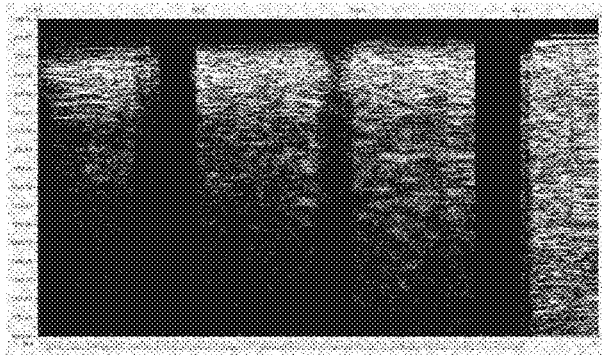
Figure 8:
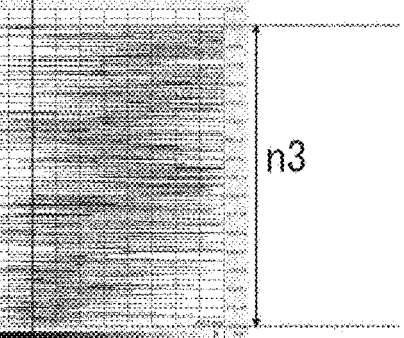

The inventors performed an experiment to verify the usability of the inspection method and apparatus according to the present invention. The experimental results are shown in FIGS. 7 and 8. In each figure, a B-scope image and an A-scope image are integrally displayed. As for test bodies shown in FIGS. 7 and 8, lining test bodies each obtained by laminating a plate-shaped steel material and polyethylene were used. At the interfaces between the steel material and the polyethylene of the respective test bodies, artificial delamination parts having different delamination widths (lengths) were formed. As for a probe, an oblique-angle probe that includes a transducer of 5 MHz and causes a longitudinal wave to have a refraction angle of 10° in steel, was used. In the example of FIG. 7, the probe interval was set to 100 mm. In the example of FIG. 8, the probe interval was set to 300 mm.

In the case of the sound part (delamination part: 0 mm) shown in (a) of FIG. 7, the range (reference detection length N) over which the echo height of the received waveform exceeded 20% (a reference value indicated by B in the figure) of the display sensitivity, was 258 mm. Meanwhile, the same range (detection length n1) with a delamination width of 20 mm shown in (b) of FIG. 7 was 311 mm, the same range (detection length n2) with a delamination width of 50 mm shown in (c) of FIG. 7 was 331 mm, and the same range (detection length n3) with a delamination width of 100 mm shown in (d) of FIG. 7 was 417 mm. Thus, in all the delamination test bodies, the ranges (detection lengths n1 to n3) over which the echo height exceeded the reference value were longer than the range (reference detection length N), of the sound test body, over which the echo height exceeded the reference value, and the echo appearance range was increased with an increase in the delamination width.

Meanwhile, FIG. 8 shows the results of an experiment performed on test bodies each having a patch plate provided at an upper portion of an artificial delamination part. In the case of a sound part (delamination part: 0 mm) shown in (a) of FIG. 8, the range (reference detection length N) over which the echo height of the received waveform exceeded 20% (reference value indicated by B in FIG. 8) of the displayed sensitivity was 730 mm. Meanwhile, the same range (detection length n1) with a delamination width of 20 mm shown in (b) of FIG. 8 was 1222 mm, the same range (detection length n2) with a delamination width of 50 mm shown in (c) of FIG. 8 was 1557 mm, and the same range (detection length n3) with a delamination width of 300 mm shown in (d) of FIG. 8 was 1600 mm or more. Also in this example, similar to the above example, in all the delamination test bodies, the range (length) over which the echo height exceeded the reference value was longer than that in the sound test body, and the echo appearance range was increased with an increase in the delamination width. Thus, it is confirmed that it is possible to determine that a delamination part is present when the echo appearance range (detection length n) is longer than that (reference detection length N) in the sound part. Besides the experiment with the probe interval of 100 mm, the inventors performed similar experiments with the probe intervals of 25, 50, 200, and 300 mm, respectively, and were able to detect delamination. Further, the inventors performed similar experiments with lining test bodies made of fluororesin and epoxy resin, respectively, instead of polyethylene, and were able to detect delamination.

Finally, the possibilities of other embodiments of the present invention will be described.

In the aforementioned embodiment, as shown in FIGS. 7 and 8, the inspection examples each using an A-scope image and a B-scope image in combination have been described. However, the image display form is not limited thereto. For example, an A-scope image and a B-scope image may be displayed independently from each other, or may be displayed to be switchable therebetween.

Figure 9:
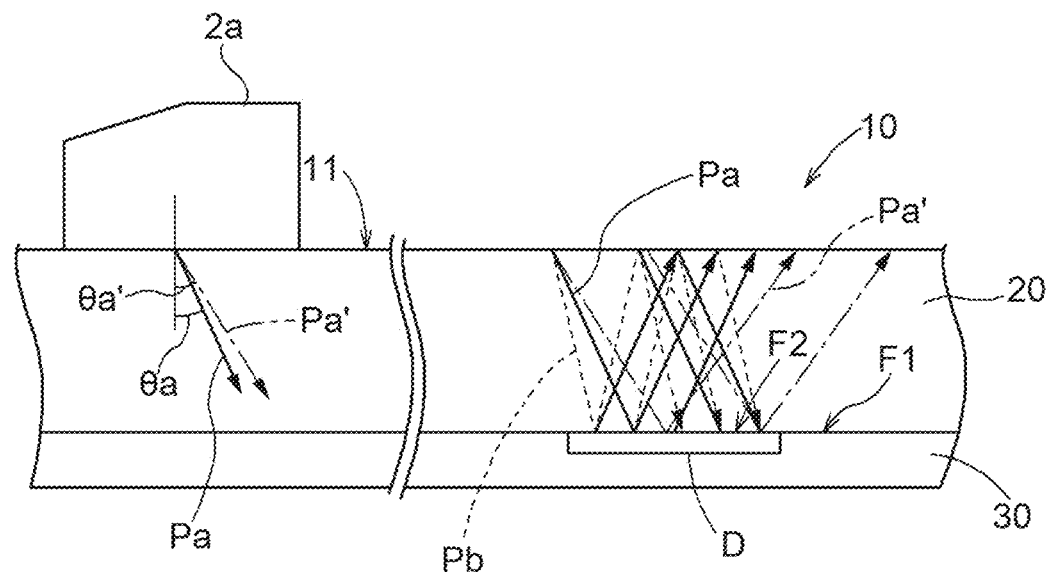
FIG. 9 is a diagram schematically showing propagation of an ultrasonic wave that is caused to enter a laminated body by a longitudinal wave angle probe.

In the aforementioned embodiment, a longitudinal wave angle probe is used as each of the transmission probe 2a and the reception probe 2b. When the longitudinal wave angle probe is used, as shown in FIG. 9, not only a longitudinal wave Pa (indicated by solid lines in FIG. 9) but also a transverse wave Pb (indicated by broken lines in FIG. 9) exists in the laminated body 10 at the same time. If the longitudinal wave Pa does not exceed its critical angle in the steel test body, the longitudinal wave Pa and the transverse wave Pb coexist in the steel test body, and are propagated so as to be mode-converted into the transverse wave Pb and the longitudinal wave Pa, respectively, while being reflected at the surface and the bottom. Therefore, the mode-converted waves, and the waves that have not been mode-converted but propagated as the original longitudinal wave and the original transverse wave, are present. Thus, the various modes of ultrasonic waves are propagated in the laminated body 10, and therefore, the difference in signals between the sound part and the delamination part becomes more distinct.

In the aforementioned embodiment, the probe that causes a longitudinal wave to have a refraction angle θ of 10° has been described as an example. However, the present invention is not limited thereto. The present invention is also applicable to a probe that causes a longitudinal wave to have a refraction angle of 5° or 2°, for example. As shown in FIG. 9, when an ultrasonic wave (propagation wave) Pa having a refraction angle θa is compared with an ultrasonic wave (propagation wave) Pa' having a refraction angle θa', the ultrasonic wave Pa having the smaller refraction angle θa has the larger number of reflections at the interface F1 between the first member 20 and the second member 30, and therefore, the number of reflections, of the ultrasonic wave Pa, at the interface F2 with the air in the delamination part D also increases. Accordingly, the smaller the refraction angle θ is, the more distinct the difference in signals between the sound part and the delamination part D. Since the ultrasonic wave transmitted from the probe is a beam having a spread, an ultrasonic wave having a refraction angle exceeding 0° exists in an ultrasonic wave beam transmitted from a normal probe. Therefore, the present invention is also applicable to a normal probe as long as such an ultrasonic wave can be observed.

In the aforementioned embodiment, as shown in FIG. 6, the scanning direction of the sensor 2 by the scanning means 4 is a direction Va perpendicular to the ultrasonic wave propagating direction (the direction in which the transmission probe 2a and the reception probe 2b oppose each other).

Figure 10:
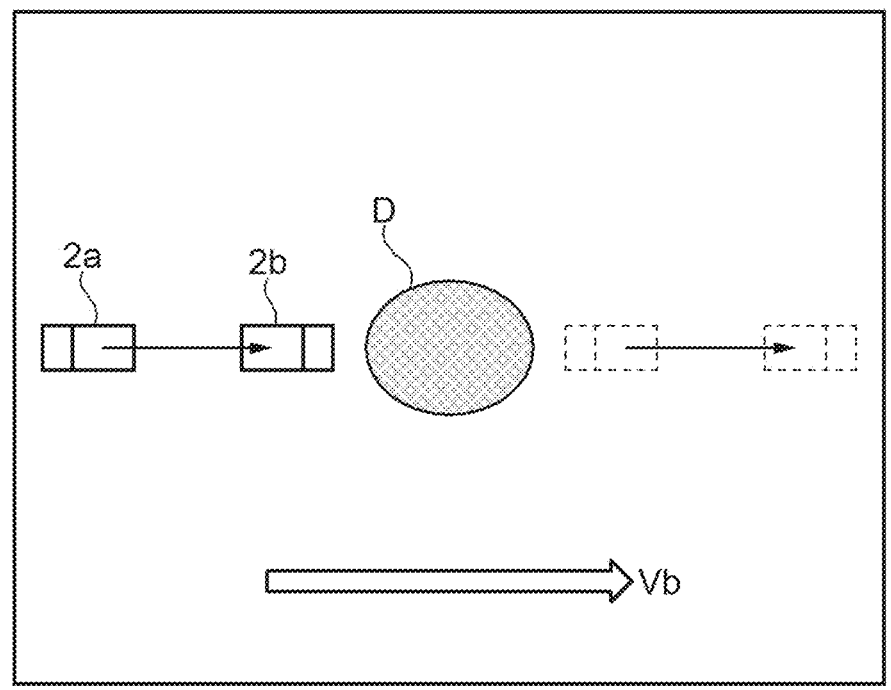
FIG. 10 is a diagram showing a sensor position and examples of measurement results, wherein (a) is a diagram showing a sensor position and a scanning direction, (b) shows an example of a B-scope image, and (c) shows an example of an A-scope image in each sensor position.

However, as shown in FIG. 10, scanning may be performed in a direction Vb identical to the propagating direction.

Incidentally, in the present invention, since the area between the transmission probe 2a and the reception probe 2b can be set as the inspection target part E, the inspection target object including the laminated body 10 is not particularly limited as long as an ultrasonic wave can be propagated between these probes.

Figure 11:
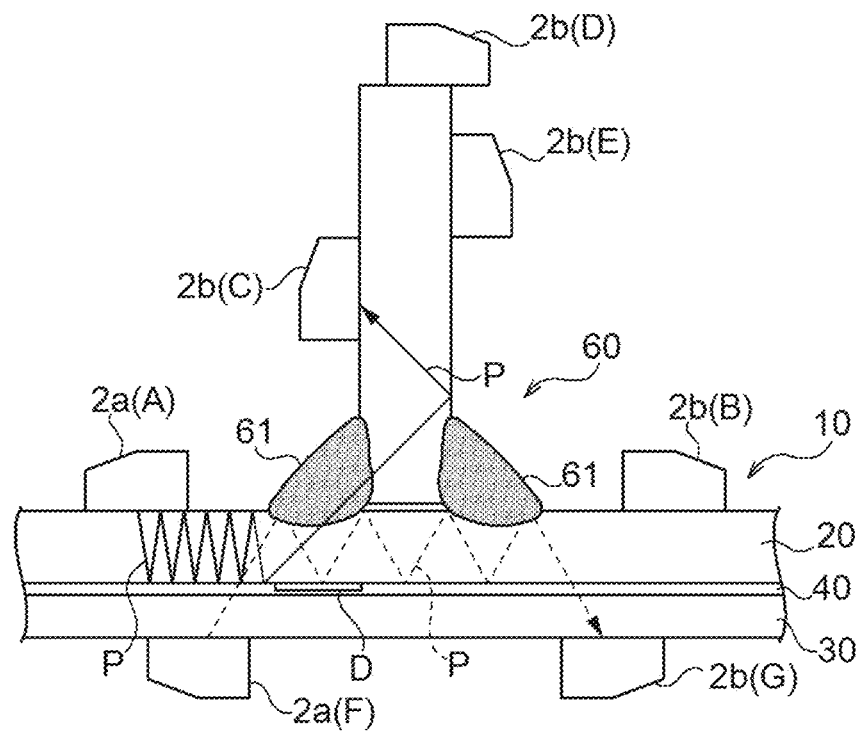
FIG. 11 is a diagram showing examples of probe arrangement with respect to a T joint.
Figure 12:
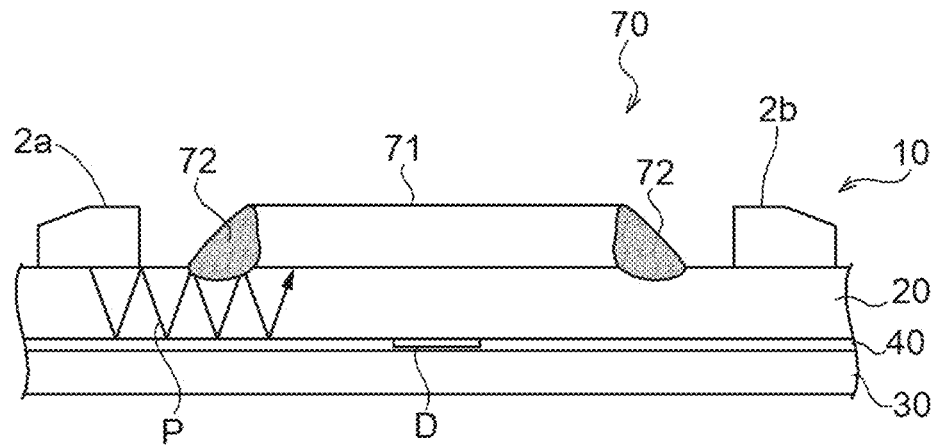
FIG. 12 is a diagram showing an example of probe arrangement with respect to a reinforcing plate.

For example, regarding arrangement of probes with respect to a T joint 60 having a welded portion 61 as shown in FIG. 11, any combination of probes, such as "A and B", "A and C", "A and D", and "A and E", may be adopted in the method of the present invention. Further, when the probes 2a and 2b are disposed on the lining member 30 side, a combination of "A and G" or "F and G" may also be adopted. Moreover, the joint having the welded portion is not limited to the T joint 60, and the present invention is also applicable to a joint 70 having a reinforcing plate 71 as shown in FIG. 12.

Figure 13:
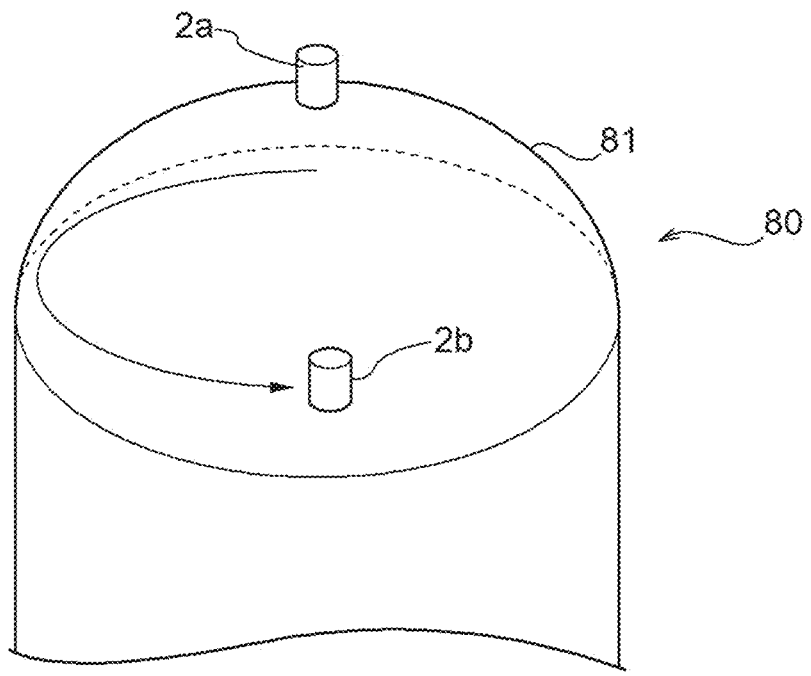
FIG. 13 is a diagram showing an example of probe arrangement on a mirror plate of a container.
Figure 14:
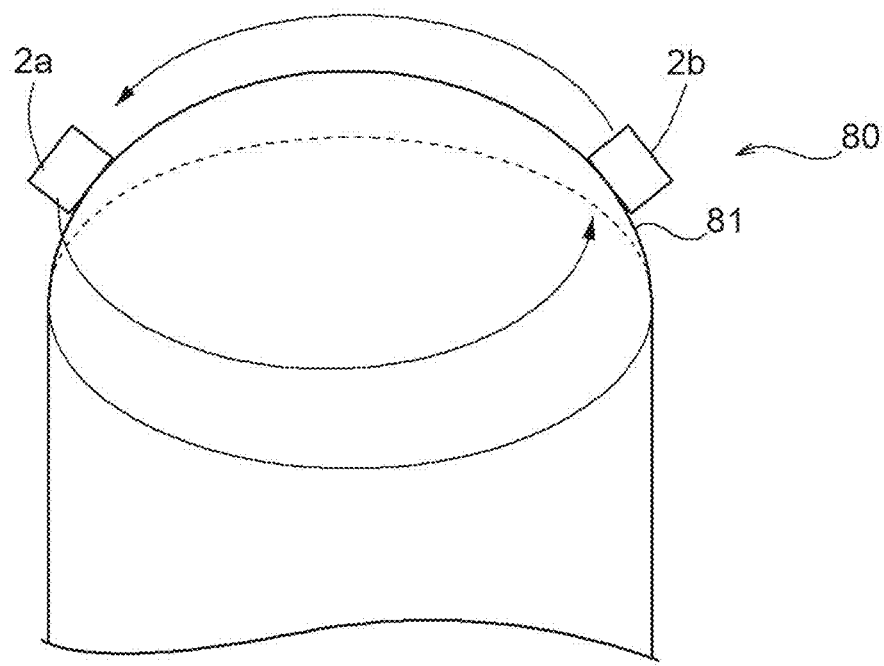
FIG. 14 is a diagram showing another example of FIG. 14.

Furthermore, as shown in FIG. 13, inspection can be simply performed by, for example, placing a normal probe as the transmission probe 2a at the top of a semi-sphere mirror plate 81 of a container 80 such as a container tank that contains a liquid composed of various chemical agents, etc., and causing only the other probe 2b to scan in the circumferential direction. In this case, the probe 2b may be either a normal probe or an oblique-angle probe. It is noted that the transmission and the reception may be inverted. Further, as shown in FIG. 14, the transmission probe 2a and the reception probe 2b may be disposed so as to oppose each other on the mirror plate 81, and may be caused to scan in the same circumferential direction while maintaining an inter-probe distance L.

Figure 15:
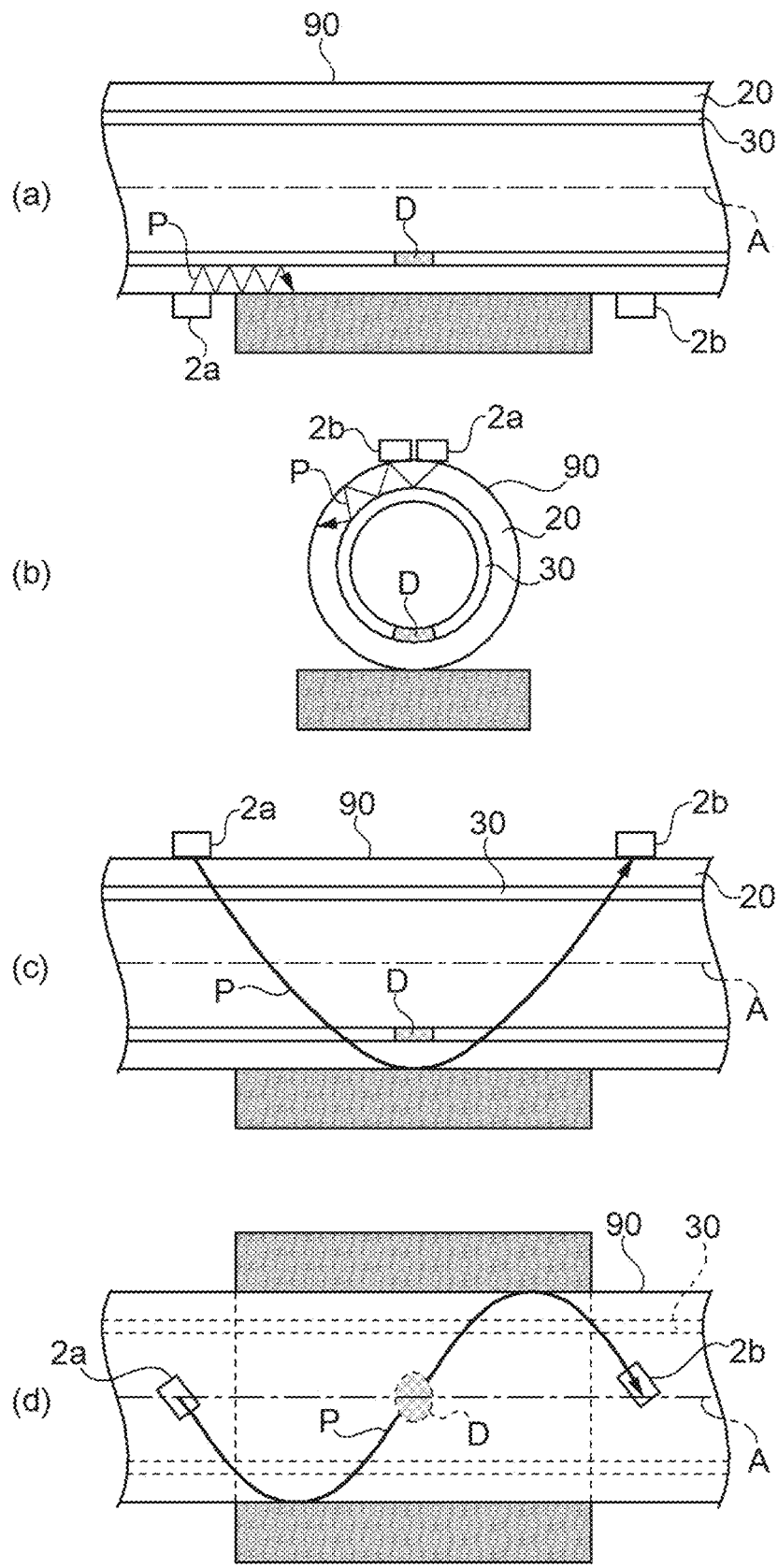
FIG. 15 is a diagram showing a delamination inspection method for a tubular body, wherein (a) shows measurement in an axial direction, (b) shows measurement in a circumferential direction, and (c) and (d) each show measurement in an oblique direction.

Furthermore, the laminated body 10 having a curved surface is not limited to the mirror plate 81 of the container 80, and may be a tubular body 90. In this case, as shown in (a) of FIG. 15, an ultrasonic wave may be propagated in a tube axis direction A of the tube 90 to detect a delamination part D. As shown in (b) of FIG. 15, an ultrasonic wave may be propagated in the circumferential direction of the tube 90 to detect the delamination part D. Further, as shown in (c) and (d) of FIG. 15, an ultrasonic wave P may be propagated in a direction (oblique direction) intersecting the tube axis direction A to detect the delamination part D.

Figure 16:
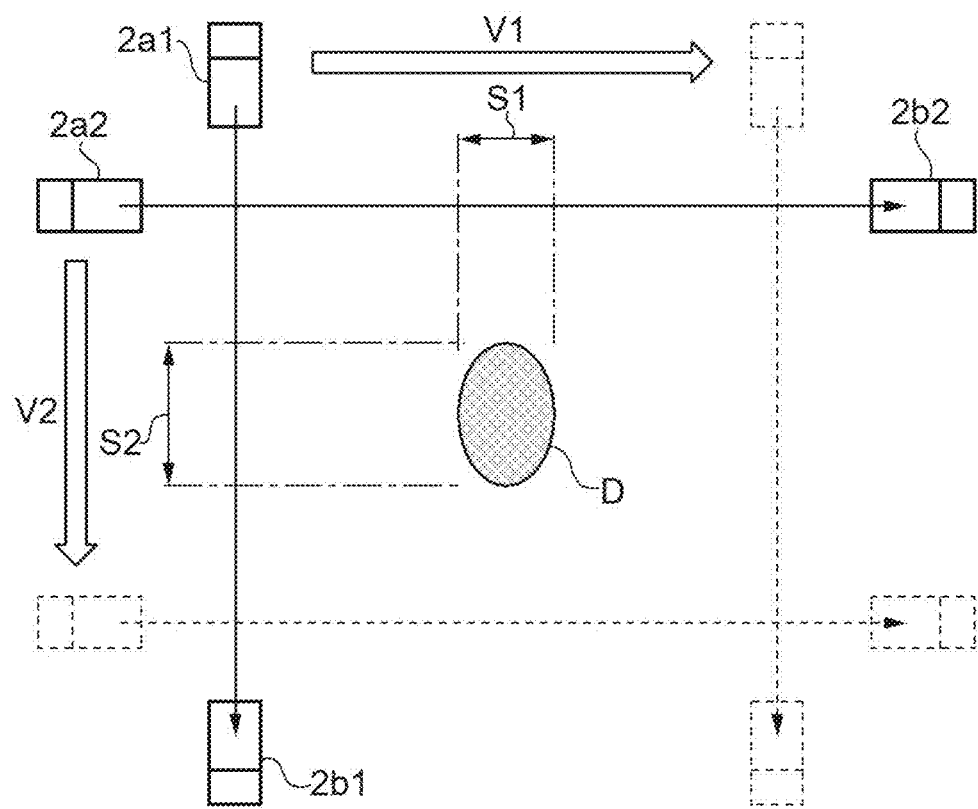
FIG. 16 is a diagram for describing how to specify the position of a delamination part by bidirectional scanning.

In the aforementioned embodiment, the sensor 2 has the paired transmission probe 2a and reception probe 2b, and detects whether or not a delamination is present between the probes 2a and 2b. Therefore, measurement (scanning) in one direction cannot specify where delamination is positioned between the probes 2a and 2b. Therefore, when the position of a delamination part D needs to be obtained, as shown in FIG. 16, for example, a first transmission probe 2a1 and a first reception probe 2b1 are caused to scan in a first scanning direction V1 to specify a delamination indicating range S1, and a second transmission probe 2a2 and a second reception probe 2b2 are caused to scan in a second scanning direction V2 perpendicular to the first scanning direction V1 to specify a delamination indicating range S2. Then, the position of the delamination part D can be specified based on an overlapping portion of the delamination indicating ranges S1 and S2. It is noted that the scanning in the two different directions (the first scanning direction V1 and the second scanning direction V2) may be performed using sensors 2 provided for the respective scanning directions as shown in FIG. 16, or may be performed using a single sensor 2 while switching the scanning direction.

INDUSTRIAL APPLICABILITY

The present invention can be used as a method and an apparatus for inspecting delamination in a laminated body, specifically, for inspecting delamination at each of interfaces of thin layers interposing between members of a storage container, piping, or the like as a laminated body obtained by laminating a plurality of members. The present invention is applicable to, for example, detection of an inter-layer delamination in a different-material laminated body obtained by, for example, adhering a CFRP material and aluminum, or adhering aluminum and copper.

DESCRIPTION OF THE REFERENCE CHARACTERS 1 delamination inspection apparatus
2 sensor
2a transmission probe
2b reception probe
2c probe holding means
3 signal processing unit
3a warning means
4 scanning means
5 pulser
6 receiver
6a preamplifier
7 filter
8 A/D converter
9 display
10 laminated body
11 one side (surface)
20 first member (plate member)
30 second member (lining member)
40 adhesive layer
50 coating film
60 T joint
61 welded portion
70 joint
71 reinforcing plate
72 welded portion
80 container
81 mirror plate
90 tubular body
A tube axis direction
B reference value
D delamination part
d delamination width (length)
E inspection target part
F1, F2 interface
N reference detection length
n detection length
P ultrasonic wave (propagation wave)
V, V1, V2, Va, Vb scanning direction
S1, S2 delamination indicating range
θ refraction angle

The invention claimed is:

1. A delamination inspection method for a laminated body, including: causing an ultrasonic wave to enter the laminated body obtained by laminating a plurality of members, from a sensor disposed on one side of the laminated body; receiving the ultrasonic wave having propagated through the laminated body; and evaluating the received ultrasonic wave to inspect whether or not an inter-layer delamination is present, the sensor including: a transmission probe configured to cause the ultrasonic wave to enter the laminated body at a predetermined refraction angle; a reception probe configured to receive a propagation wave having propagated while having been repeatedly reflected by interfaces of the plurality of members; and a probe holding means configured to hold the transmission probe and the reception probe with a predetermined interval therebetween, and the method comprising:

disposing the transmission probe and the reception probe on a sound part of the laminated body, with a preset probe interval therebetween by using the probe holding means, receiving the propagation wave having propagated through the sound part, and obtaining, as a reference detection length, a detection length over which an echo height of the received propagation wave through the sound part is detected as being equal to or greater than a predetermined value;

disposing the transmission probe and the reception probe so as to sandwich an inspection target part of the laminated body with an interval same as the preset probe interval by using the probe holding means, receiving the propagation wave having propagated through the inspection target part, and measuring a measured detection length over which an echo height of the received propagation wave through the inspection target part is detected as being equal to or greater than the predetermined value; and comparing the measured detection length with the reference detection length to inspect whether or not an inter-layer delamination is present in the inspection target part.

2. The delamination inspection method for the laminated body according to claim 1, wherein the transmission probe and the reception probe are disposed so as to sandwich another member provided on the laminated body.

3. The delamination inspection method for the laminated body according to claim 2, wherein each of the transmission probe and the reception probe is a longitudinal wave angle probe.

4. The delamination inspection method for the laminated body according to claim 1, wherein each of the transmission probe and the reception probe is a longitudinal wave angle probe.

5. The delamination inspection method for the laminated body according to claim 1, wherein the sensor further includes a scanning means configured to cause the transmission probe and the reception probe to scan the laminated body.

6. The delamination inspection method for the laminated body according to claim 3, wherein a scanning image is generated based on the propagation wave having propagated through the inspection target part.

7. The delamination inspection method for the laminated body according to claim 1, wherein the sensor further includes a first scanning means configured to cause the transmission probe and the reception probe to scan along a first scanning direction, and a second scanning means configured to scan along a second scanning direction intersecting the first scanning direction, and the position of the inter-layer delamination is specified through the scanning of the first scanning means and the second scanning means.

8. The delamination inspection method for the laminated body according to claim 7, wherein a scanning image is generated based on the propagation wave having propagated through the inspection target part.

9. The delamination inspection method for the laminated body according to claim 1, wherein the transmission probe and the reception probe are disposed on a curved surface of the laminated body.

10. The delamination inspection method for the laminated body according to claim 9, wherein at least the transmission probe is a normal probe, and the normal probe is fixed to a top of the curved surface while the reception probe is caused to scan in a circumferential direction with respect to the transmission probe.

11. The delamination inspection method for the laminated body according to claim 10, wherein the laminated body is a mirror plate portion of a container.

12. The delamination inspection method for the laminated body according to claim 9, wherein the laminated body is a mirror plate portion of a container.

13. The delamination inspection method for the laminated body according to claim 9, wherein the laminated body is a tubular body.

14. The delamination inspection method for the laminated body according to claim 1, wherein the plurality of members include at least a first member positioned at the one side, a second member provided on the first member, and an adhesive layer adhering these members.

15. The delamination inspection method for the laminated body according to claim 14, wherein the first member is a steel member, and the second member is a lining member.

16. The delamination inspection method for the laminated body according to claim 14, wherein the first member is a lining member, and the second member is a steel member.

17. A delamination inspection apparatus for a laminated body including a signal processing unit configured to cause an ultrasonic wave to enter the laminated body obtained by laminating a plurality of members, from a sensor disposed on one side of the laminated body, receive the ultrasonic wave having propagated through the laminated body, and evaluate the received ultrasonic wave to inspect whether or not an inter-layer delamination is present, the sensor including: a transmission probe configured to cause the ultrasonic wave to enter the laminated body at a predetermined refraction angle; a reception probe configured to receive a propagation wave having propagated while having been repeatedly reflected by interfaces of the plurality of members; and a probe holding means configured to hold the transmission probe and the reception probe with a predetermined interval therebetween, and the signal processing unit being configured to:

while the transmission probe and the reception probe are disposed on a sound part of the laminated body with a preset probe interval therebetween maintained by the probe holding means, receive the propagation wave having propagated through the sound part, and obtain a detection length, as a reference detection length, over which an echo height of the received propagation wave through the sound part is detected as being equal to or greater than a predetermined value;

while the transmission probe and the reception probe sandwich an inspection target part of the laminated body with an interval that is the same as the preset probe interval and maintained by the probe holding means, receive the propagation wave having propagated through the inspection target part, and measure a measured detection length over which an echo height of the received propagation wave through the inspection target part is detected as being equal to or greater than the predetermined value; and compare the measured detection length with the reference detection length to inspect whether or not an inter-layer delamination is present in the inspection target part.

18. The delamination inspection apparatus for the laminated body according to claim 17, wherein the signal processing unit generates a scanning image on the basis of the propagation wave having propagated through the inspection target part.

* * * * *